United States Patent [19]

Costales et al.

[11] Patent Number: 5,763,359
[45] Date of Patent: Jun. 9, 1998

[54] N-(1-ETHYL-4-PYRAZOLYL) TRIAZOLOAZINESULFONAMIDE HERBICIDES

[75] Inventors: Mark J. Costales; William A. Kleschick; Robert J. Ehr, all of Indianapolis; Monte R. Weimer, Pittsboro, all of Ind.

[73] Assignee: Dow AgroSciences LLC, Indianapolis, Ind.

[21] Appl. No.: 703,165

[22] Filed: Aug. 28, 1996

Related U.S. Application Data

[60] Provisional application No. 60/003,086, Aug. 31, 1995.
[51] Int. Cl.[6] .................. A01N 43/54; A01N 43/653; C07D 403/14; C07D 401/14
[52] U.S. Cl. .................. 504/251; 504/246; 544/256; 546/118
[58] Field of Search .................. 504/241, 246; 544/256; 546/118

[56] References Cited

U.S. PATENT DOCUMENTS

| | | | |
|---|---|---|---|
| 4,818,273 | 4/1989 | Kleschick et al. | 71/90 |
| 5,163,995 | 11/1992 | Van Heertum et al. | 504/241 |
| 5,177,206 | 1/1993 | Johnson et al. | 544/263 |
| 5,201,938 | 4/1993 | Costales et al. | 504/241 |
| 5,447,905 | 9/1995 | Costales et al. | 504/241 |
| 5,494,887 | 2/1996 | Johnson et al. | 504/241 |
| 5,571,775 | 11/1996 | Van Heertum et al. | 504/246 |

FOREIGN PATENT DOCUMENTS 244948  11/1987  European Pat. Off. .

*Primary Examiner*—Matthew V. Grumbling
*Attorney, Agent, or Firm*—D. Wendell Osborne

[57] ABSTRACT

Substituted N-(1-ethyl-4-pyrazolyl) triazoloazinesulfonamide compounds, such as N-(1-ethyl-5-methyl-3-(trifluoromethyl)-4-pyrazoyl)-5-methoxy-7-methyl-[1,2,4]triazolo[1,5-c]pyrimidine-2-sulfonamide and N-(1-ethyl-5-methyl-3-(trifluoromethyl)-4-pyrazolyl)-5-methoxy-7-methyl[1,2,4]triazolo[1,5-a]pyridine-2-sulfonamide, were prepared and found to possess selective herbicidal utility. The compounds are especially useful for the preemergence control of grassy weeds in soybeans

29 Claims, No Drawings

N-(1-ETHYL-4-PYRAZOLYL) TRIAZOLOAZINESULFONAMIDE HERBICIDES

CROSS-REFERENCE TO RELATED APPLICATIONS

This application claims the benefit of U.S. Provisional application Ser. No. 60/003,086, filed Aug. 31, 1995.

BACKGROUND OF THE INVENTION

The present invention relates to substituted sulfonamide compounds, to herbicidal compositions containing the compounds, and to the utility of the compounds for the control of unwanted vegetation.

The control of unwanted vegetation by means of chemical agents, i.e., herbicides, is an important aspect of modern agriculture and land management. While many chemicals that are useful for the control of unwanted vegetation are known, new compounds that are more effective generally, are more effective for specific plant species, are less damaging to desirable vegetation, are safer to man or the environment, are less expensive to use, or have other advantageous attributes are desirable.

Certain substituted N-(1-methyl-4-pyrazolyl)-[1,2,4]triazolo[1,5-c]pyrimidine-2-sulfonamide compounds and their herbicidal utility have been disclosed in U.S. Pat. No. 5,201,938. The activity of these compounds on certain weeds especially grassy weeds, and the selectivity of these compounds to certain desired crops, such as soybeans, are not sufficient to permit them to be used for the control of weeds in these crops. A large number of herbicidal N-(substituted phenyl)[1,2,4]-triazolo[1,5-c]pyrimidine-2-sulfonamide compounds were disclosed in U. S. Pat. No. 5,163,995. Certain substituted N-(1-methyl-4-pyrazolyl)[1,2,4]triazolo-[1,5-a]pyrimidine-2-sulfonamide compounds and their herbicidal utility were disclosed in U.S. Pat. No. 4,954,163.

SUMMARY OF THE INVENTION

It has now been found that certain N-(1-ethyl-4-pyrazolyl) triazoloazinesulfonamide compounds, including certain N-(1-ethyl-4-pyrazolyl)[1,2,4]triazolo[1,5-c]pyrimidine-2-sulfonamide compounds and certain N-(1-ethyl-4-pyrazolyl)[1,2,4]triazolo[1,5-a]pyridine-2-sulfonamide compounds, are potent herbicides for the control of unwanted vegetation including grassy weeds, have surprisingly good crop selectivity to broadleaf crops including soybeans, and have favorable toxico-logical and environmental attributes.

The invention includes N-(1-ethyl-4-pyrazolyl)-triazoloazine-2-sulfonamide compounds of Formula I:

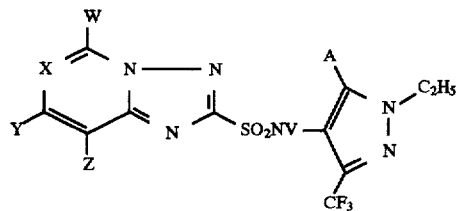

wherein

A represents H, $CH_3$, $OCH_3$, Cl, or Br; and

V represents H, $CO(C_1-C_4)$alkyl optionally singly to completely substituted with fluorine, $CO_2(C_1-C_4)$alkyl, $CO_2(C_3-C_4)$alkenyl, $CO_2(C_3-C_4)$alkynyl, $CONH(C_1-C_4)$alkyl or $CON((C_1-C_4)$alkyl$)_2$;

and either (a)

W represents $OCH_3$ or $OC_2H_5$;

X represents CH or N; and one of Y and Z represents Cl, Br, I, $OCH_3$, or $CH_3$ and the other represents H;

or (b)

W and Y each represents H;

X represents C—Q and Q represents Cl, Br, I, $OCH_3$, or $CH_3$; and

Z represents $OCH_3$ or $OC_2H_5$; and when V represents H, the agriculturally acceptable salts thereof.

The compounds of the invention, usually in the form of an herbicidal composition containing one or more of them in admixture with an agriculturally acceptable adjuvant or carrier, exhibit herbicidal properties on a broad spectrum of undesirable vegetation when applied either directly to the unwanted vegetation or to the locus thereof, and when applied either preemergence or postemergence. They are especially useful for the control of grassy weeds and are usually most advantageously employed for the selective control of such weeds in broadleaf crops, such as soybeans. It is typically preferred to apply the compounds preemergence to achieve selective control.

The compounds are advantageously employed in combination with complementary herbicides that are useful for the control of broadleaf weeds in broadleaf crops.

DETAILED DESCRIPTION OF THE INVENTION

The N-(1-ethyl-4-pyrazolyl)triazoloazinesulfonamide compounds of the invention can be characterized as [1,2,4]triazolo[1,5-c]pyrimidine-2-sulfonamide compounds and [1,2,4]triazolo[1,5-a]pyridine-2-sulfonamide compounds possessing an alkoxy substituent in the 5-position and a methyl, methoxy, or halogen substituent in one of the 7- and 8-positions or, in the case of [1,2,4]triazolo[1,5-a]pyridine-2-sulfonamide compounds, an alkoxy substituent in the 8-position and a methyl, methoxy or halogen substituent in the 6-position, and further possessing, on the sulfonamide nitrogen atom, a 1-ethyl-4-pyrazolyl moiety substituted with a trifluoromethyl group in the 3-position and, optionally, with a methyl, methoxy, chloro, or bromo substituent in the 5-position The compounds are amides derivable from either a substituted [1,2,4]triazolo[1,5-c]pyrimidine-2-sulfonic acid compound (X represents N) or a [1,2,4]triazolo[1,5-a]pyridine-2-sulfonic acid compound (X represents CH or C—Q) and an optionally substituted 4-amino-1-ethyl-3-(trifluoromethyl)pyrazole compound.

The compounds of the invention include those of Formula I:

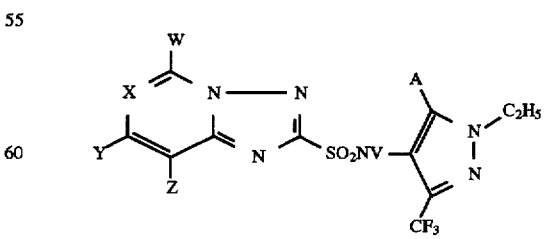

wherein X represents N, CH, or C—Q. Compounds wherein X represents N, which are [1,2,4]triazolo[1,5-c]pyrimidine-2-sulfonamide compounds, are usually preferred, but in some circumstances compounds wherein X represents CH or C—Q, which are [1,2,4]triazolo[1,5-a]pyridine-2-sulfonamide compounds, are preferred.

The compounds of Formula I wherein X represents N or CH are substituted in the 5-position (W) with a methoxy or ethoxy substituent and compounds wherein X represents C—Q are substituted in the 8-position (Z) with a methoxy or ethoxy substituent. Methoxy is often preferred, but ethoxy is sometimes preferred. When X represents N or CH, the compounds possess an additional substituent in the 7-position (Y) or 8-position (Z) of the [1,2,4]triazoloazine heterocycle, which substituent may be selected from methyl, chloro, bromo, iodo, and methoxy. Such compounds wherein there is an additional methyl, chloro, bromo, or methoxy substituent in the 7-position or wherein there is an additional methoxy substituent in the 8-position are often preferred. Compounds wherein there is an additional methyl substituent in the 7-position, an additional chloro substituent in the 7-position, or an additional methoxy substituent in the 8-position are, separately, sometimes of special interest. 7-Methyl compounds are most preferred. When X represents C—Q, the 5-position (W) and 7-position (Y) are unsubstituted (W and Y represent hydrogen) and the 6-position (Q) substituent is a methyl, chloro, bromo, iodo, or methoxy group.

The pyrazole ring of the compounds of Formula I possesses an ethyl substituent in the 1-position and a trifluoromethyl substituent in the 3-position and is attached to the sulfonamide nitrogen at the 4-position. It may be substituted in the 5-position (A) with methyl, methoxy chloro, or bromo. Compounds wherein A represents methyl or methoxy are often preferred and those wherein A represents methyl are typically more preferred.

The term V in Formula I represents hydrogen, $CO(C_1–C_4)$ alkyl optionally singly to completely substituted with fluorine, $CO_2(C_1–C_4)$alkyl, $CO_2(C_3–C_4)$-alkenyl, $CO_2(C_3–C_4)$alkynyl, $CONH(C_1–C_4)$alkyl, or $CON((C_1–C_4)$alkyl$)_2$. Hydrogen is typically preferred. Compounds wherein V is other than hydrogen typically hydrolyze in a plant or in the environment to form the corresponding compound wherein V represents hydrogen When V represents hydrogen, the compounds of Formula I are acidic and the invention includes the agriculturally acceptable salts.

The term alkyl as used herein includes straight chain, branched chain, and cyclic moieties. Thus, typical alkyl groups are methyl, ethyl, 1-methylethyl, propyl, cyclopropyl and the like. Methyl and ethyl are often preferred. Typical alkyl groups singly to completely substituted with fluorine include trifluoromethyl, monofluoromethyl, 2,2,2-trifluoroethyl, 2,3-difluoropropyl, and the like; trifluoromethyl is often preferred.

The term "agriculturally acceptable salts" is employed herein to denote compounds wherein the acidic sulfonamide proton of the compound of Formula I is replaced by a cation which itself is neither herbicidal to crop plants being treated nor significantly deleterious to the applicator, the environment, or the ultimate user of any crop being treated. Suitable cations include, for example, those derived from alkali or alkaline earth metals and those derived from ammonia and amines. Preferred cations include sodium, potassium, magnesium, and aminium cations of the formula:

$$R^6R^7R^8NH^+$$

wherein $R^6$, $R^7$, and $R^8$ each independently represents hydrogen or $(C_1–C_{12})$alkyl, $(C_3–C_{12})$cycloalkyl, or (C3–$C_{12}$)alkenyl, each of which is optionally substituted by one or more hydroxy, $(C_1–C_8)$alkoxy, $(C_1–C_8)$alkylthio or phenyl groups; provided that $R^6$, $R^7$, and $R^8$ are sterically compatible. Additionally, any two of $R^6$, $R^7$, and $R^8$ together may represent an aliphatic difunctional moiety containing 1 to 12 carbon atoms and up to two oxygen or sulfur atoms. Salts of the compounds of Formula I can be prepared by treatment of compounds of Formula I wherein V represents hydrogen with a metal hydroxide, such as sodium hydroxide, potassium hydroxide, or magnesium hydroxide, or an amine, such as ammonia, trimethylamine, hydroxyethylamine, bisallylamine, 2-butoxyethylamine, morpholine, cyclododecylamine, or benzylamine.

A listing of some typical compounds of the invention is given in Table 1. Some of the specifically preferred compounds of the invention include the following: N-(1-ethyl-5-methyl-3-(trifluoromethyl)-4-pyrazolyl)-5,8-dimethoxy [1,2,4]triazolo[1,5-c]-pyrimidine-2-sulfonamide, N-(1-ethyl-5-methyl-3-(trifluoromethyl)-4-pyrazolyl)-5-methoxy-7-methyl[1,2,4]triazolo[1,5-c]pyrimidine-2-sulfonamide, N-(1-ethyl-5-methoxy-3-(trifluoromethyl)-4-pyrazolyl)-5-methoxy-7-methyl[1,2,4]triazolo[1,5-c]pyrimidine-2-sulfonamide, N-(1-ethyl-5-methyl-3-(trifluoromethyl)-4-pyrazolyl)-7-chloro-5-methoxy[1,2,4]triazolo[1,5-c]pyrimidine-2-sulfonamide, N-(1-ethyl-5-methyl-3-(trifluoromethyl)-4-pyrazolyl)-5-ethoxy-7-methyl [1,2,4]triazolo[1,5-c]-pyrimidine-2-sulfonamide, N-(1-ethyl-5-methyl-3-(trifluoromethyl)-4-pyrazolyl)-5-methoxy-7-methyl[1,2,4]-triazolo[1,5-a]pyridine-2-sulfonamide, and N-(1-ethyl-5-methyl-3-(trifluoromethyl)-4-pyrazolyl)-5-ethoxy-7-methyl[1,2,4]triazolo[1,5-a]pyridine-2-sulfonamide.

TABLE 1

N-(N-ETHYL-4-PYRAZOLYL)TRIAZOLOAZINESULFONAMIDE COMPOUNDS

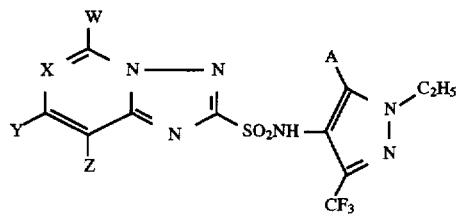

| Cpd. No. | W | X | Y | Z | A | B | Form | Melting point, °C. | % C calc. found | % H calc. found | % N calc. found | % S calc. found |
|---|---|---|---|---|---|---|---|---|---|---|---|---|
| 1 | OCH₃ | N | CH₃ | H | CH₃ | CF₃ | white powder | 208–209 | 40.1 / 40.3 | 3.85 / 3.67 | 23.4 / 23.4 | 7.64 / 7.49 |
| 2 | OCH₃ | CH | CH₃ | H | CH₃ | CF₃ | white solid | 230–231 | 43.1 / 43.3 | 4.10 / 4.29 | 20.1 / 20.2 | 7.66 / 7.79 |
| 3 | OCH₃ | CH | H | Br | CH₃ | CF₃ | tan powder | 250–251 (d) | 34.8 / 35.2 | 2.92 / 3.13 | 17.4 / 17.5 | 6.64 / 6.35 |
| 4 | OC₂H₅ | CH | CH₃ | H | CH₃ | CF₃ | tan solid | 233–235 | 44.4 / 44.7 | 4.43 / 4.03 | 19.4 / 18.9 | 7.41 / 6.81 |
| 5 | OCH₃ | CH | CH₃ | H | OCH₃ | CF₃ | white solid | 220–221 | 42.9 / 42.6 | 4.27 / 4.73 | 18.7 / 18.1 | 7.15 / 6.63 |
| 6 | OC₂H₅ | CH | CH₃ | H | OCH₃ | CF₃ | off-white solid | 216–218 | 41.5 / 42.1 | 3.94 / 3.71 | 19.4 / 19.0 | 7.38 / NT |
| 7 | OCH₃ | N | H | OCH₃ | CH₃ | CF₃ | off-white solid | 208–210 (d) | 38.6 / 38.5 | 3.70 / 3.87 | 22.5 / 22.2 | 7.36 / 7.09 |
| 8 | OCH₃ | N | H | I | CH₃ | CF₃ | dk. orange solid | 190–193 (d) | 29.4 / 29.5 | 2.47 / 2.52 | 18.5 / 18.5 | 6.04 / 5.56 |
| 9 | OCH₃ | N | H | Br | CH₃ | CF₃ | lt. yellow solid | 185–187 (d) | 32.2 / 31.9 | 2.71 / 2.88 | 20.3 / 20.0 | 6.62 / 6.14 |
| 10 | OC₂H₅ | N | CH₃ | H | CH₃ | CF₃ | off-white solid | 209–210 (d) | 41.6 / 41.8 | 4.19 / 4.20 | 22.6 / 22.4 | 7.39 / 7.03 |
| 11 | OCH₃ | N | Cl | H | CH₃ | CF₃ | yellow solid | 174–176 (d) | 35.5 / 35.7 | 2.98 / 2.83 | 22.3 / 22.2 | 7.29 / 7.21 |
| 12 | H | C—Cl | H | OCH₃ | CH₃ | CF₃ | off-white solid | 245–247 (d) | 38.3 / 38.1 | 3.22 / 3.29 | 19.1 / 18.9 | 7.31 / 6.99 |
| 13 | OCH₃ | N | CH₃ | H | H | CF₃ | white solid | 193–194 | 38.5 / 38.4 | 3.48 / 3.76 | 24.2 / 23.9 | 7.91 / 7.70 |
| 14 | OCH₃ | N | H | Cl | CH₃ | CF₃ | lt. yellow solid | 190–192 (d) | 35.5 / 36.6 | 2.98 / 3.12 | 22.3 / 21.7 | 7.29 / 7.46 |
| 15 | OCH₃ | N | CH₃ | H | OCH₃ | CF₃ | off-white solid | 196–198 (d) | 38.6 / 38.9 | 3.70 / 3.79 | 22.5 / 22.2 | 7.36 / 7.16 |
| 16 | OCH₃ | N | CH₃ | H | Cl | CF₃ | light tan solid | 191–193 (d) | 35.5 / 35.8 | 2.98 / 2.70 | 22.3 / 22.6 | 7.29 / — |
| 17 | OC₂H₅ | N | CH₃ | H | Cl | CF₃ | off-white solid | 200–202 (d) | 37.1 / 38.2 | 3.33 / 3.14 | 21.6 / 20.4 | 7.06 / — |
| 18 | OCH₃ | N | H | Cl | Cl | CF₃ | off-white solid | 193–196 (d) | 31.3 / 31.5 | 2.19 / 2.13 | 21.3 / 20.9 | 6.97 / 6.95 |

The compounds of Formula I wherein V represents hydrogen can generally be prepared by combining a 2-chlorosulfonyltriazoloazine compound (a 2-chlorosulfonyl[1,2,4]triazolo[1,5-c]pyrimidine compound when X represents N or a 2-chlorosulfonyl[1,2,4]triazolo[1,5-a]-pyridine compound when X represents CH or C—Q) of Formula II:

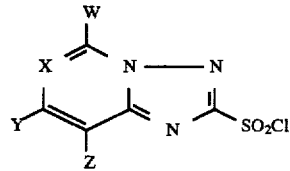

(wherein W, X, Y, and Z are as defined for compounds of Formula I) with an appropriate 4-amino-1-ethyl-3-(trifluoromethyl)pyrazole compound of Formula III:

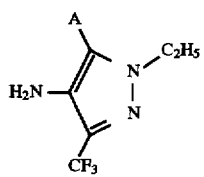

(wherein A is as defined for compounds of Formula I) in the presence of pyridine or a methylpyridine compound, and, optionally but preferably, a catalytic amount of dimethyl sulfoxide.

The preparation is usually accomplished by combining the 2-chlorosulfonyltriazoloazine compound of Formula II; the 4-amino-1-ethylpyrazole compound of Formula III and an inert solvent, such as acetonitrile, N,N-dimethylformamide; N-methyl-2-pyrrolidinone, tetrahydrofuran, and the like, in a vessel and then adding the pyridine or methylpyridine, preferably pyridine, and a catalytic amount of dimethyl sulfoxide. The mixture is allowed to react, typically at ambient temperature, but with heating, if necessary. After a substantial quantity of the compound of Formula I has formed or a substantial quantity of the chlorosulfonyl compound of Formula II has been consumed, the desired product is recovered, typically by removing the solvent by evaporation, adding water; and removing the liquids from the solid that forms by filtration or centrifugation. The product recovered can be purified, if desired, by extracting with an immiscible organic solvent, such as dichloromethane, and with water. Alternatively, the desired compounds of Formula I can be purified by recrystallization and by other commonly used methods.

Approximately equimolar quantities of the compounds of Formulas II and III are generally used in the preparation of compounds of Formula I although a substantial excess of one or the other may be employed. The pyridine or methylpyridine compound is generally employed in an amount of from at least 1 to about 5 moles per mole of compound of Formula II. Dimethyl sulfoxide is typically used in less than an equimolar amount; amounts over about 0.2 mole per mole of compound of Formula II are usually deleterious. Acetonitrile is often the preferred solvent.

It is sometimes advantageous to prepare the compounds of Formula I by condensing a chlorosulfonyl compound of Formula II with an N-trialkylsilyl derivative of a substituted 4-amino-1-ethylpyrazole compound of Formula III The method employed is analogous to that described in U.S. Pat. No. 4,910,306 for N-trialkylsilylanilines. The reaction conditions required are essentially the same as those described hereinabove for the condensation of a compound of Formula II with an aminopyrazole compound of Formula III with the exception that the pyridine compound base may be omitted. The substituted N-trialkylsilyl-4-amino-1-ethylpyrazole compounds employed can be prepared from the corresponding substituted 4-amino-1-ethylpyrazole compounds by treatment with a trialkylsilyl halide and a trialkylamine as described in U.S. Pat. No. 4,910,306 for aniline compounds Sodium iodide is typically employed as a catalyst when the halide is chloride. The N-trialkylsilyl-4-amino-1-ethyl-3-(trifluoromethyl)pyrazole compounds are typically prepared and used immediately and without purification.

Compounds of Formula I wherein W represents methoxy or ethoxy and wherein V represents hydrogen can be made from the corresponding compounds related to those of Formula I wherein W represents chloro by treatment with an appropriate alkoxide reagent, such as sodium methoxide in methanol. The reaction conditions employed are similar to those used for the related exchange reactions of 2- and 4-chloropyrimidines. Non-aqueous media are preferred. Selective replacement of chlorine in the 5-position (W) can readily be achieved as this chlorine is much more reactive than chlorine in the 7- and 8- positions (Y and Z). Similarly, compounds of Formula I wherein Z represents methoxy or ethoxy and wherein V represents hydrogen can be made from the corresponding compounds wherein Z represents chloro.

Compounds of Formula I wherein V represents $CO(C_1-C_4)$alkyl optionally singly to completely substituted with fluorine, $CO_2(C_1-C_4)$alkyl, $CO_2(C_3-C_4)$-alkenyl, $CO_2(C_3-C_4)$alkynyl, $CONH(C_1-C_4)$alkyl, or $CON((C_1-C_4)$alkyl$)_2$ can be prepared from compounds of Formula I wherein V represents hydrogen by acylation with the corresponding acid chloride compound using conventional procedures known in the art for the acylation of sulfonamides.

The 2-chlorosulfonyl[1,2,4]triazolo[1,5-c]-pyrimidine compounds of Formula II and their analogs wherein the W represents chloro can be prepared by the methods taught in U.S. Pat. No. 5,010,195. The 2-chlorosulfonyl [1,2,4]triazolo[1,5-a]pyridine compounds of Formula II and their analogs wherein W represents chloro can be prepared in an analogous manner. The method generally involves the chloroxidation of a 2-benzylthio compound of Formula IV:

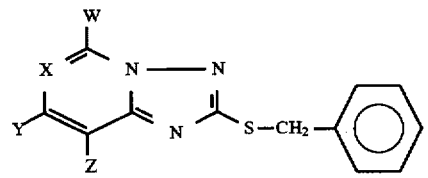

wherein W, X, Y, and Z are defined as for compounds of Formula I and, in addition, when X represents N or CH, W represents Cl and when X represents C—Q, Z represents Cl. Typically, the compounds of Formula IV are placed in a mixture of dichloromethane and water and chlorine gas is added with stirring and cooling to keep the temperature below about 30° C. When the reaction is complete, the phases are separated and the organic solution phase is concentrated by evaporation under reduced pressure to obtain the desired compound of Formula II as a residue. The intermediate is typically used without further purification.

Compounds of Formula IV wherein X represents N can be prepared by the methods taught in U.S. Pat. No. 5,010,195. The preparation of Formula IV compounds wherein X represents CH or C—Q is described in the Examples.

The preparation of the substituted 4-amino-1-ethyl-3-(trifluoromethyl)pyrazole intermediates of Formula II is described in the Examples.

While it is possible to utilize the N-(1-ethyl-4-pyrazolyl) triazoloazinesulfonamide compounds of Formula I directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations which are normally diluted with additional carriers and adjuvants before application. They can be solids, such as, for example dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic or non-ionic in character and can be employed as emulsifying agents, wetting agents, suspending agents, or for other purposes. Typical surface active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products; such as tridecyl alcohol-$C_{16}$ ethoxylate, soaps, such as sodium stearate; alkylnaphthalenesulfonate; salts, such as sodium dibutylnaphthalenesulfonate; dialkyl esters of sulfosuccinate salts such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters Other adjuvants commonly used in agricultural compositions include antifoam agents, compatibilizing agents, sequestering agents, neutralizing agents and buffers, corrosion inhibitors, dyes, odorants, penetration aids, spreading agents, sticking agents, dispersing agents, thickening agents, freeze point depressants, antimicrobial agents, and the like. The compositions can also contain other compatible components, for example; other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight Concentrations from about 0.01 to about 90 percent by weight are often employed. In compositions designed to be employed as concentrates, the active ingredient is generally present in a concentration from about 5 to about 98 weight percent, preferably about 10 to about 90 weight percent Such compositions are typically diluted with an inert carrier, such as water, before application. The diluted compositions usually applied to weeds or the locus of weeds generally contain about 0.001 to about 5 weight percent active ingredient and preferably contain about 0.01 to about 0.5 percent.

The present compositions can be applied to weeds or their locus by the use of conventional ground or aerial dusters, sprayers, and granule applicators, by addition to irrigation water, and by other conventional means known to those skilled in the art.

The compounds of Formula I have been found to be useful preemergence and postemergence herbicides. The compounds can be employed at non-selective (higher) rates of application to control essentially all of the vegetation in an area or, in some cases, at selective (lower) rates of application for the selective control of undesirable vegetation in crops, especially broadleaf crops, such as soybeans and cotton. Grassy weeds are especially well controlled at lower rates of application. The selective control of grassy weed in soybeans is of special interest and is most evident when the compounds are applied preplant or preemergence. While each of the N-(1-ethyl-4-pyrazolyl) triazoloazinesulfonamide compounds encompassed by Formula I is within the scope of the invention the degree of herbicidal activity, the degree of crop selectivity, and the spectrum of weed control obtained varies depending upon the substituents present.

The compounds of the present invention (Formula I) are best applied in conjunction with one or more other herbicides to obtain control of a wider variety of undesirable vegetation. Since the compounds of Formula I are generally more potent on grassy weeds than on broadleaf weeds, other herbicides that are especially potent on broadleaf weeds are typically employed in this embodiment When used in conjunction with other herbicides, the presently claimed compounds can be formulated with the other herbicide or herbicides, tank mixed with the other herbicide or herbicides, or applied sequentially with the other herbicide or herbicides. Some of the herbicides that can be employed in conjunction with the compounds of the present invention include substituted triazolopyrimidinesulfonamide compounds, such as N-(2,6-dichlorophenyl)-5-ethoxy-7-fluoro[1,2,4]triazolo[1,5-c]pyrimidine-2-sulfonamide (diclosulam), N-(2-methoxycarbonyl-6-chlorophenyl)-5-ethoxy-7-fluoro[1,2,4]triazolo[1,5-c]pyrimidine-2-sulfonamide (cloransulam-methyl), and N-(2,6-difluorophenyl)-5-methyl[1,2,4]triazolo[1,5-a]pyrimidine-2-sulfonamide (flumetsulam). Other herbicides such as acifluorfen, bentazon, chlorimuron, clomazone, fumiclorac, fluometuron, fomesafen, imazaquin, imazethapyr, lactofen, linuron, metribuzin, and others can also be employed. It is generally preferred to use the compounds in conjunction with a broadleaf herbicide that is selective to cotton or soybeans and is applied preemergence. It is further generally preferred to apply the compounds at the same time, either as a combination formulation or as a tank mix.

The compounds of the present invention can generally be employed in combination with known herbicide safeners, such as cloquintocet, furilazole, dichlormid, benoxacor, flurazole, and fluxofenim, to enhance their selectivity. They can additionally be employed to control undesirable vegetation in many crops that have been made tolerant to or resistant to herbicides by genetic manipulation or by mutation and selection. For example, corn, wheat, rice, soybean, sugarbeet, cotton, canola, and other crops that have been made tolerant or resistant to herbicides that inhibit acetolactate synthase in sensitive plants can be treated.

The term herbicide is used herein to mean an active ingredient which controls or adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation are meant to include germinant seeds., emerging seedlings and established vegetation Herbicidal activity is exhibited by the compounds of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote selective or non-selective herbicidal action.

Application rates of about 0.001 to about 1 Kg/Ha are generally employed in postemergence operations; for preemergence applications, rates of about 0.01 to about 10

Kg/Ha are generally employed. The higher rates designated generally give non-selective control of a broad variety of undesirable vegetation, the lower rates are generally employed for selective control in the presence of a crop. Preemergence applications are generally preferred

EXAMPLES

The following Examples are presented to illustrate the various aspects of this invention and should not be construed as limitations to the claims.

1. Preparation of 1-Ethyl-5-methyl-3-(trifluoromethyl) pyrazole

A solution of 25.0 g (grams) (167 mmol) (millimoles) of ethylhydrazine oxalate in 50 mL (milliliters) of ethanol was added to a solution of 25.0 g (162 mmol) of 1,1,1-trifluoro-2,4-pentanedione in 200 mL of ethanol at ambient temperature with stirring. The mixture was heated to reflux with stirring for 18 hours and was then allowed to cool. The volatile components were removed by evaporation under reduced pressure and the residue obtained was taken up in 150 mL of dichloromethane. The resulting solution was washed twice with 100 mL portions of water, dried over magnesium sulfate, filtered, and concentrated by evaporation under reduced pressure to obtain 19.1 g (66 percent of theory) of the title compound as an amber oil Elemental Analysis $C_7H_9F_3N_2$ Calc.: % C, 47.2; % H, 5.09; % N, 15.7 Found: % C, 47.3; % H, 4.87; % N, 15.9

$^1$H NMR (CDCl$_3$): 6.18(s, 1H), 4.05(q, 2H, J=8.0), 2.23(s, 3H), 1.35(t, 3H, J=8.0).

2. Preparation of 1-Ethyl-5-methyl-4-nitro-3-(trifluoromethyl)pyrazole

A mixture of 30 mL of concentrated sulfuric acid and 30 mL of concentrated nitric acid was added slowly with stirring at 0° C. to a solution of 18.9 g (106 mmol) of 1-ethyl-5-methyl-3-(trifluoromethyl)pyrazole in 70 mL of concentrated sulfuric acid. When the addition was complete, the mixture was allowed to warm to ambient temperature and stir for 72 hours. It was then poured slowly onto 500 g of ice. The resultant mixture was extracted twice with 100 mL portions of dichloromethane. The combined extracts were dried over magnesium sulfate, filtered, and concentrated by evaporation under reduced pressure to obtain 20.4 g (86 percent of theory) of the title compound as a yellow oil.

Elemental Analysis $C_7H_8F_3N_3O_2$ Calc.: % C, 37.7; % H, 3.61; % N, 18.8 Found: % C, 37.6; % H, 3.67; % N, 19.1

$^1$H NMR (CDCl$_3$): 4.18(q, 2H, J=7.3), 2.64(s, 3H), 1.44(t, 3H, J=7.3).

3. Preparation of 4-Amino-1-ethyl-5-methyl-3-(trifluoromethyl)pyrazole

A mixture of 18.9 g (84.7 mmol) of 1-ethyl-5-methyl-4-nitro-3-(trifluoromethyl)pyrazole, 100 mL of ethanol, and 300 mg (milligrams) of 5 percent palladium on carbon catalyst was prepared in a Parr® shaker bomb flask and was placed under 50 pounds per square inch (3445 kiloPascals) of pressure with hydrogen. The mixture was shaken until 21 pounds per square inch (1447 kilopascals) of hydrogen had been absorbed and then the hydrogen was replaced with nitrogen. The catalyst was removed by filtration and the volatiles were removed by evaporation under reduced pressure. The resulting amber oil was simple distilled to obtain 7.8 g (48 percent of theory) of the title compound as a clear, colorless liquid boiling at 70°–71° C. at 0.2 millimeters mercury (27 Pascals) pressure.

Elemental Analysis $C_7H_{10}F_3N_3$ Calc.: % C, 43.5; % H, 5.22; % N, 21.8 Found: % C, 44.0; % H, 5.71; % N, 21.7

$^1$H NMR (CDCl$_3$): 4.05(q, 2H, j=7.4), 2.97(brs, 2H), 2.16(s, 3H), 1.37(t, 3H, J=7.4).

4. Preparation of 1-Ethyl-5-hydroxy-3-(trifluoromethyl) pyrazole

A mixture of 45.0 g of potassium carbonate and 50.0 g (272 mmol) of ethyl 4,4,4-trifluoroacetoacetate in 300 mL of ethanol was cooled with a salt/ice bath to about 0° C. and to this ethylhydrazine oxalate (44.9 g, 299 mmol) was added with a spatula with stirring. After 45 min (minutes) at about 0° C., the mixture was allowed to warm to ambient temperature and stir for 1 hour. It was then heated to reflux overnights The mixture was concentrated by evaporation under reduced pressure and the residue was diluted with dichloromethane and water. The product only partially dissolved and seemed to be distributed in both phases. The layers were separated and the aqueous layer was extracted with dichloromethane and filtered. The solids obtained on filtration were extracted with dichloromethane. The dichloromethane layers and extracts were combined, washed with water (2×200 mL), and dried and the volatiles were allowed to evaporate overnight. All of the solids were combined to obtain the title compound.

Elemental Analysis $C_6H_7F_3N_2O$ Calc.: % C, 40.0; % H, 3.92; % N, 15.6 Found: % C, 37.4; % H, 3.83; % N, 14.4

$^1$H NMR (DMSO-d$_6$): 1.26(t, 3H, J=7.2), 3.93(q, 2H, J=7.2), 4.15(bs, 1H); 5.66(s, 1H); $^{13}$C NMR (DMSO-d$_6$): 14.31, 41.32, 84.25, 121(bq), 137.9(q), 152.83.

5. Preparation of 1-Ethyl-5-methoxy-3-(trifluoromethyl) pyrazole

A solution of 37.1 g (206 mmol) of 1-ethyl-5-hydro-y-3-(trifluoromethyl)pyrazole in 500 mL of methanol was prepared and to this was added dropwise with stirring at ambient temperature 47.1 mL of 25 percent sodium methoxide in methanol (206 mmol). The mixture, which was exothermic, was allowed to react for about 1 hour and then 19.5 mL (206 mmol) of dimethyl sulfate was added dropwise with stirring at ambient temperature. After about 1 hour, this mixture was heated at reflux with stirring overnight. Some starting material appeared to be present (gas chromatographic analysis) so another 0.3 equivalent of dimethyl sulfate and 0.1 equivalent of sodium methoxide in methanol were added and the mixture was heated at reflux with stirring overnight. The mixture was concentrated by evaporation under reduced pressure to obtain a light yellow residue. This was diluted with 250 mL of dichloromethane and 150 mL of water and the layers were separated The aqueous layer was extracted with dichloromethane (3×50 mL). The combined dichloromethane layers were washed with water (3×100 mL), dried over magnesium sulfate, and concentrated by evaporation under reduced pressure to obtain a yellow oil which partially solidified on standing several days. The solids were removed by filtration and extracted with a little dichloromethane. The resulting oil was distilled and the fraction boiling at 39°–42° C. at 5 mm Hg (700 Pascals) was collected to obtain 15.8 g of the title compound as a clear liquid.

Elemental Analysis $C_7H_9F_3N_2O$ Calc.: % C, 43.3; % H, 4.67; % N, 14.4 Found: % C, 38.1; % H, 4.43; % N, 13.1

$^1$H NMR (CDCl$_3$) 1.34(t, 1H, J=7.3), 3.88(s, 3H), 3.79(q, 2H, J=7.3), 5.74(s, 1H).

6. Preparation of 1-Ethyl-5-methoxy-4-nitro-3-(trifluoromethyl)pyrazole

1-Ethyl-5-methoxy-3-(trifluoromethyl)pyrazole (15.2 g, 0.0785 mmol) was added dropwise with stirring and cooling at about 0° C. to 150 mL of concentrated sulfuric acid and then 10.5 mL of 70 percent nitric acid (0.235 mmol) was added, also dropwise with stirring at about 0° C. The mixture was then allowed to warm to ambient temperature and stir overnight. An aliquot was removed, neutralized to a pH of about 11, extracted with dichloromethane, and analyzed by gas chromatography. Since there was still some starting material present another about 0.8 mmol of concentrated nitric acid was added with stirring and the mixture was allowed to react for 5 hours. Analysis of an aliquot as before did not reveal any remaining starting material so the mixture was poured slowly into 500 g of ice. The mixture was stirred for 15 min and was then extracted with dichloromethane (4×200 mL). The extracts were combined to obtain an acidic blue-green organic mixture. This was diluted with 100 mL of water and neutralized with 50 percent aqueous sodium hydroxide. The mixture, which turned yellow-orange, was separated into phases and the organic layer was dried over magnesium sulfate, filtered, and concentrated under reduced pressure to obtain 12.4 g of the title compound as a yellow oil.

$^1$H NMR (CDCl$_3$): 1.46(t, 3H, J=7.3), 4.12(q, 2H, J=7.3), 4.25(s, 3H); $^{13}$C NMR (CDCl$_3$): 14.47, 43.86, 63.79, 103.39, 120.0(bq), 135.3(q), 151.1.

7. Preparation of 4-Amino-1-ethyl-5-methoxy3-(trifluoromethyl)pyrazole

A solution of 12.4 g (51.9 mmol) of 1-ethyl-5-methoxy-4-nitro-3-(trifluoromethyl)-5-pyrazole in 150 mL of ethanol was prepared in a Parr® shaker bomb and 0.30 g of 10 percent palladium on carbon catalyst was added. The mixture was pressured to 12.75 pounds per square inch gauge (1890 kiloPascals) with hydrogen while shaking and allowed to react for 2 days. It was then filtered through powdered cellulose to remove the catalyst and the yellow solution obtained, which darkened quickly on exposure to air, was concentrated by evaporation under reduced pressure to obtain the desired product in impure form as a purple oil.

$^1$H NMR (CDCl$_3$): 1.34(t, 3H, J=7.3), 2.8(bs, 2H), 3.94(s, 3H), 3.95(q, 2H, j=7.3).

8. Preparation of 5-Chloro-1-ethyl-3-(trifluoromethyl) pyrazole-4-carboxaldehyde Dimethylformamide (13.36 g 182.7 mmol) was cooled to about 0° C. and 60.69 g (395.8 mmol) of phosphoryl chloride was added dropwise with stirring to form a pink slurry. This was allowed to warm to ambient temperature and then 32.92 g (182.7 mmol) of 1-ethyl-5-hydroxy-3-(trifluoromethyl)pyrazole was added dropwise with stirring to it. There appeared to be an endotherm and the mixture became dark brown to black. The mixture was then heated at reflux (108° C.) overnight and, after cooling, was poured into an ice-water mixture with stirring. A precipitate formed and then dissolved. The solution was extracted with dichloromethane (3×150 mL) and the combined extracts were dried over magnesium sulfate, filtered, and concentrated under reduced pressure to obtain the title compound as a dark brown to black oil.

Element Analysis C$_7$H$_6$F$_3$ClN$_2$O Calc.: % C, 37.1; % H, 2.67 Found: % C, 37.0; % H, 2.70

$^1$H NMR (CDCl$_3$): 1.46(t, 3H, J=7.3), 4 25(q, 2H, J=7.3), 9.91(s, 1H).

9. Preparation of 5-Chloro-1-ethyl-3-(trifluoromethyl) pyrazole-4-carboxylic Acid A mixture of 29.5 g (131 mmol) of 5-chloro-1-ethyl-3-(trifluoromethyl)-pyrazole-4-carboxaldehyde in 350 mL of distilled water was prepared and 0.733 g (131 mmol) of potassium hydroxide and 20.6 g (131 mmol) of potassium permanganate were added to it. The mixture was heated to 60° C. with stirring for 2 hours. The color turned from purple to dark brown. An aliquot was taken, filtered to remove the solids, acidified, and analyzed by gas chromatography to determine that the reaction was complete. The reaction mixture was then filtered to remove the solids and the filtrate was acidified to pH 2. The precipitate that formed was recovered by filtration and washed with water to obtain a white solid. This solid was partially dissolved in hot dichloromethane and the insoluble portion removed by gravity filtration. The filtrate was concentrated by evaporation under reduced pressure to obtain 23.4 g of the title compound as a white solid melting at 164°–166° C.

Elemental Analysis C$_7$H$_6$F$_3$ClN$_2$O$_2$ Calc.: % C 34.7; % H, 2.49; % N, 11.6 Found: % C,34.9; % H, 2.56; % N, 11.7

$^1$H NMR (CDCl$_3$): 1.44(t, 3H, J=7.3), 4.27(q, 2H, J=7.3), 11.4(bs, 1H).

10. Preparation of 5-Chloro-1-ethyl-3-(trifluoromethyl) pyrazol-4-carboxamide

A mixture of 22.5 g (91.6 mmol) of 5-chloro-1-ethyl-3-(trifluoromethyl)pyrazole-4-carboxylic acid and 45 mL of thionyl chloride was prepared and heated to reflux with stirring for 3 hours. The slurry became a dark orange solution. The excess thionyl chloride and other volatiles were removed by evaporation under reduced pressure to obtain a dark brown oil. This was taken up in 250 mL of dichloromethane and the resulting solution was cooled to about 0° C. and treated with 100 mL of concentrated ammonium hydroxide, which was added dropwise with stirring and cooling. When the addition was complete, the mixture was allowed to warm to ambient temperature and stir over a 2-hour period. The solids were collected by filtration and washed with water (3×50 mL). The solids that formed in the filtrate due to evaporation of the dichloromethane were collected in the same way. The combined solids were washed with water (2×100 mL) and were then suspended in water for 2 hours, recollected by filtration, and dried in an oven under reduced pressure. The white solid obtained was 18.4 g of the title compound melting at 15°–152° C.

Elemental Analysis C$_7$H$_7$F$_3$ClN$_3$O Calc.: % C, 34.8; % H, 2.92; % N, 17.4 Found: % C, 34.8; % H, 2.97; % N, 17.6

$^1$H NMR (CDCl$_3$): 1.45(t, 3H, J=7.3), 4.24(q, 2H, J=7.3), 5.9(bs, 2H).

11. Preparation of 4-Amino-5-chloro-1-ethyl-3-(trifluoromethyl)pyrazole

A mixture of 17.9 g (74.1 mmol) of 5-chloro-1-ethyl-3-(trifluoromethyl)pyrazole-4-carboxamide and 250 mL of methanol was cooled to about 0° C. and to it was added dropwise with stirring and cooling first 48.0 g (222 mmol) of a 25 percent sodium methoxide in methanol solution and then a solution of 11.8 g (74.1 mmol) of bromine in 40 mL of methanol. The mixture was stirred at about 0° C. for 1 hour, allowed to warm to ambient temperature over a 2-hour period, and then heated at reflux overnight. The mixture was allowed to cool and was concentrated by evaporation under reduced pressure to obtain an off-white to tan solid. This solid was suspended in 350 mL of 1N aqueous sodium hydroxide solution and the mixture heated at reflux with stirring for 3 hours. The mixture was allowed to cool and was then extracted with dichloromethane (3×150 mL). The aqueous phase was acidified with 2N aqueous hydrochloric acid and was then reextracted with dichloromethane (3×100 mL). The dichloromethane extracts were combined, dried over magnesium sulfate, and concentrated by evaporation under reduced pressure to obtain the title compound as a brown oil containing some dichloromethane.

Elemental Analysis C$_6$H$_7$F$_3$ClN$_3$ Calc.: % C, 33.7; % H, 3.30; % N, 19.7 Found: % C, 29.7; % H, 3.68; % N, 17.0

$^1$H NMR (CDCl$_3$): 1.41(t, 3H, J=7.3), 3.33(bs, 2H), 4.14(q, 2H, J=7.3).

12. Preparation of 2-Benzylthio-5-hydroxy-7-methyl[1,2,4]triazolo[1,5-a]pyridine A mixture of thiosemicarbazide (50.0 g, 0.554 mol) and benzyl chloride (67.1 g, 0.53 mol) in 2-propanol (1 L) was heated to reflux with stirring for 2 hours. The reaction mixture was then cooled and 4-methyl-glutaconic anhydride (60.8 g, 0.482 mol) and triethyl-amine (75 mL, 53.6 g 0.53 mol) were added. The reaction mixture was again heated at reflux with stirring for an hour. Sodium methoxide in methanol solution (250 mL of 25 percent, 1.09 mol) was then added and the yellow-brown mixture obtained was heated at reflux with stirring for 2.5 hours. The volatiles were removed by evaporation under reduced pressure and the residue obtained was combined with dilute aqueous acetic acid (150 mL) and ethyl acetate. The organic phase was recovered, washed well with water and concentrated by evaporation under reduced pressure. The residue obtained was heated with a heat gun under reduced pressure for 30 min until the bubbling had stopped and the reaction mixture had solidified. The mixture was cooled and diluted with methanol and the resulting solids were recovered by filtration to obtain 54.5 g (41 percent of theory) of the title compound as a yellow-brown powder melting at 214°–216° C.

Elemental Analysis $C_{13}H_{11}ClN_4S$ Calc.: % C, 62.0; % H, 4.83; % N, 15.5; % S, 11.9 Found: % C, 61.9; % H, 4.88; % N, 15.5; % S, 11.5

13. Preparation of 2-Benzylthio-5-chloro-7-methyl[1,2,4]triazolo[1,5-a]pyridine

N,N-Dimethylaniline (21.9 g, 0.18 mol) was added slowly to a mixture of 2-benzylthio-5-hydroxy-7-methyl[1,2,4]triazolo[1,5-a]pyridine (44.5 g, 0.164 mol) in 150 mL of phosphorus oxychloride with stirring. The mixture was heated at reflux with stirring for 20 hours. The excess phosphorus oxychloride was then removed by evaporation under reduced pressure. The residue obtained was dissolved in ethyl acetate, washed well with water and quickly concentrated by evaporation under reduced pressure to drive off the excess water. The residue was again dissolved in ethyl acetate and the resulting mixture was filtered with suction through a bed of silica gel. The filtrate was concentrated by evaporation under reduced pressure and the residue obtained was mixed with hexane. The resulting mixture was filtered to recover the solids and dried to obtain the 37.5 g (79 percent of theory) of the title compound as a tan powder melting at 108°–110° C.

Elemental Analysis $C_{14}H_{12}ClN_3S$ Calc.: % C, 58.0; % H, 4.17; % N, 14.5; % S, 11.1 Found: % C, 58.4; % H, 3.93; % N, 14.6; % S, 11.0

$^1$H NMR (CDCl$_3$): 7.20–7.52(m, 6H), 6.86(s, 1H), 4.51(s, 2H), 2.44(s, 3H); $^{13}$C NMR (CDCl$_3$): 165.4, 152.5, 141.7, 131.2, 129.1, 128.4, 128.1, 127.3, 115.2, 112.2, 35.8, 21 4.

14. Preparation of 2-Benzylthio-5-methoxy-7-methyl[1,2,4]triazolo[1,5-a]pyridine A mixture of 2-benzylthio-5-chloro-7-methyl[1,2,4]triazolo[1,5-a]pyridine (5.0 g, 0.017 mol), sodium methoxide in methanol (16 mL of 25 percent, 3.7 g, 0.070 mol) and methanol (100 mL) were heated at reflux with stirring for 4 hours. The reaction mixture was then cooled, acidified with acetic acid (10 mL), and concentrated by evaporation under reduced pressure. The residue obtained was dissolved in dichloromethane and the resulting solution was washed well with water, dried over magnesium sulfate, and concentrated by evaporation under reduced pressure. The residue obtained was mixed with hexane and filtered to recover the solids. The solids were dried to obtain 4.7 g (97 percent of theory) of the title compound as a tan powder melting at 85°–87° C.

Elemental Analysis $C_{15}H_{15}N_3OS$ Calc.: % C, 63.1; % H, 5.30; % N, 14.7; % S, 11.2 Found: % C, 62.9; % H, 5.12; % N, 14.7; % S, 11.3

$^1$H NMR (CDCl$_3$): 7.24–7.46(m, 5H), 7.02(s, 1H), 6.06(s, 1H), 4.51(s, 2H), 4.10(s, 3H), 2.43(s, 3H).

15. Preparation of 2-Hydrazino-3-nitropyridine

2-Chloro-3-nitropyridine (100 g, 0.63 mol), hydrazine monohydrate (70.4 mL, 72.6 g, 1.45 mol) and methanol (1.3 L) were mixed and heated to reflux with stirring. After 30 min the reaction mixture was cooled and filtered collecting the insoluble materials. The filtrate was concentrated by evaporation under reduced pressure and the residue obtained as well as the insoluble materials from the filtration were diluted with water. The insoluble solids present were collected by filtration, washed with water, and dried to obtain 95.2 g (98 percent of theory) of the title compound as a bright yellow powder melting at 168°–169° C.

Elemental Analysis $C_5H_6N_4O_2$ Calc.: % C, 39.0; % H, 3.90; % N, 36.4; % S, 8.27 Found: % C, 39.1; % H, 4.17; % N, 36.1; % S, 8.18

16. Preparation of 2-Benzylthio-8-nitro[1,2,4]triazolo[1,5-a]pyridine

2-Hydrazino-3-nitropyridine (95.2 g, 0.618 mol) was combined with acetonitrile (1 L) and carbon disulfide (114 mL, 143.9 g, 1.89 mol) was added. The resulting mixture was stirred for 1.5 hours. Hydrogen peroxide (78.6 mL of 30 percent aqueous solution, 23.6 g, 0.693 mol) was added dropwise over a 20-min period with cooling at 15°–20° C. The mixture was stirred for another 2 hours and was then cooled in an ice bath. Benzyl chloride (91.7 g, 0.72 mol) was added and then triethylamine (110 mL, 79.6 g, 0.79 mol) was added slowly with stirring over a 2-hour period. The reaction was exothermic. The mixture was stirred at room temperature over the weekend. The volatiles were removed by evaporation under reduced pressure and the residue obtained was diluted with dichloromethane and water. The resulting mixture was filtered through Celite® to remove the precipitated sulfur. The organic phase of the filtrate was recovered, washed with water, and concentrated by evaporation under reduced pressure. The solid residue obtained was diluted with hexane, recovered by filtration, and dried to obtain 174.0 g (98 percent of theory) of the title compound as a brown powder melting at 125°–126° C. (d).

Elemental Analysis $C_{13}H_{10}N_4O_2S$ Calc.: % C, 54.5; % H, 3.52; % N, 19.6; % S, 11.2 Found: % C, 54.8; % H, 3.64; % N, 19.7; % S, 11.3

17. Preparation of 8-Amino-2-benzylthio-[1,2,4]triazolo[1,5-a]pyridine

2-Benzylthio-8-nitro[1,2,4]triazolo[1,5-a]pyridine (174.0 g, 0.61 mol), iron filings (204.2 g, 3.65 mol) and acetic acid (2 L) were combined and heated with stirring at 70°–80° C. for 6 hours. The reaction mixture was cooled and diluted with water and dichloromethane. The resulting mixture was filtered through Celite®, the liquid phases in the filtrate were separated, and the aqueous layer was extracted with a little more dichloromethane. The organic phase and extract were combined and washed several times with water and then with dilute aqueous sodium hydroxide. The resulting organic solution was concentrated by evaporation under reduced pressure and the residue obtained was mixed with ether. The insoluble solids were collected by filtration and dried to obtain 106.3 g of the title compound as a brown powder melting at 116°–117° C. An additional 14.2 g of lower purity product was isolated from the ether filtrate (77 percent of theory total yield). This reduction was also carried out with iron powder and calcium chloride in aqueous ethanol and with stannous chloride in hydrochloric acid.

18. Preparation of 8-Amino-2-benzylthio-5,7-dichloro[1,2,4]triazolo[1,5-a]pyridine 8-Amino-2-benzylthio[1,2,4]triazolo[1,5-a]pyridine (20.0 g, 0.078 mol), N-chlorosuccinimide (10.4 g 0.078 mol) and carbon tetrachloride were combined and heated to reflux with stirring for 1 hour. The reaction mixture was cooled, another 10.4 g of N-chlorosuccinimide was added, and the reaction heated to reflux with stirring for another hour. The reaction mixture was then cooled and filtered. The filtrate was concentrated by evaporation under reduced pressure and the residue obtained was purified by column chromatography on silica gel eluting with dichloromethane. The product fractions were concentrated by evaporation under reduced pressure and the residues were combined and mixed with ether. The insoluble solids were collected by filtration and dried to obtain 18.0 g (71 percent of theory) of the title compound as a light tan powder melting at 118°–119° C.

19. Preparation of 2-Benzylthio-5,7-dichloro[1,2,4]triazolo[1,5-a]pyridine

8-Amino-2-benzylthio-5,7-dichloro[1,2,4]triazolo[1,5-a]pyridine (25.8 g, 0.079 mol), t-butyl nitrite (18.9 mL, 16.4 g, 0.158 mol) and tetrahydrofuran (1.5 L) were combined and heated at reflux with stirring. Gas evolution began immediately and stopped after a few minutes, but the reaction was heated at reflux for an hour. The volatiles were removed by evaporation under reduced pressure and the residue obtained was chromatographed on silica gel eluting with dichloromethane. The product fractions were concentrated by evaporation under reduced pressure and the residue obtained was mixed with ether. The insoluble solid material was collected by filtration. The ether filtrate was concentrated by evaporation under reduced pressure and the residue was rechromatographed on silica gel eluting with 10 percent ethyl acetate in hexane. The product fractions were concentrated by evaporation under reduced pressure and the residue obtained was combined with the insoluble solid material obtained before to obtain 12.2 g (50 percent of theory) of the title compound as a red-brown powder melting at 88°–89° C.

Elemental Analysis $C_{13}H_9Cl_2N_3S$ Calc: % C, 50.3; % H, 2.92; % N, 13.6; % S, 10.3 Found: % C, 50.1; % H, 2.92; % N, 13.6; % S, 10.2

2-Benzylthio-5,7-dibromo[1,2,4]triazolo[1,5-a]pyridine was prepared similarly from 8-amino-2-benzylthio-5,7-dibromo[1,2,4]triazolo[1,5-a]pyridine. A 32 percent yield of this compound was obtained as a light tan powder melting at 113°–114° C.

20. Preparation of 8-Amino-2-benzylthio-5-chloro[1,2,4]triazolo[1,5-a]pyridine A solution of 8-amino-2-benzylthio[1,2,4]triazolo[1,5-a]pyridine (14.0 g, 0.0546 mol) and 1,3-dichloro-5,5-dimethylhydantoin (5.4 g, 0.0273 mol) were combined in 500 mL of dichloromethane and the mixture was heated at reflux with stirring for two hours. Additional 1,3-dichloro-5,5-dimethylhydantoin (5.0 g, 0.025 mol) was added and the reaction was heated with stirring for an additional hour. The reaction mixture was cooled and dilute aqueous sodium bisulfite was added with stirring and allowed to react for an hour. The mixture was then washed with water and the volatiles were removed by evaporation under reduced pressure. The residue obtained was chromatographed on silica gel eluting with dichloromethane to obtain 6.0 g (38 percent of theory) of the title compound as a light tan powder melting at 113°–114° C.

Elemental Analysis $C_{13}H_{11}ClN_4S$ Calc.: % C, 53.7; % H, 3.81; % N, 19.3; % S, 11.0 Found: % C, 53.9; % H, 3.84; % N; 19.5; % S, 11.0

21. Preparation of 1,2-Diamino-3,5-dichloropyridinium Mesitylate

2-Amino-3,5-dichloropyridine (9.48 g, 58.1 mmol) was dissolved in chloroform (100 mL) in a round bottom flask and the mixture was cooled to 5° C. in an ice bath. To this mixture was added dropwise with stirring a freshly prepared solution of O-mesitylenesulfonylhydoxylamine (15.5 g, 69.8 mmol) in chloroform. (warning; this compound is an explosive solid). A thick white precipitate began to form after 15 min. The mixture was allowed to warm to room temperature while stirring overnight. The solids present were recovered by filtration, washed with chloroform (3×100 mL), and dried to obtain 17.5 g (80 percent of theory) of the title compound as a white crystalline solid melting at 231°–232° C.

Infrared Analysis (KBr): 3407, 3203, 3025, 2936, 1656, 1369, 1182, 1086, 1014, 679, 600, 548 cm$^{-1}$;

$^1$H NMR (DMSO-d$_6$): 8.81(s, 2H), 8.42(s, 2H), 7.01(s,, 2H), 6.73(s, 2H), 2.50(s, >6H), 2.16(s, 3H).

1,2-Diamino-3,5-dibromopyridinium mesitylate was prepared similarly and was obtained in 92 percent yield as an off-white solid melting at 212°–213° C.

$^1$H NMR (DMSO-d$_6$): 8.67(brs, 2H), 8.58(d, 1H, J=2.1), 8.47 (d, 1H, J=2.1), 6.99(s, 2H), 6.74(s, 2H), 2.49(s, >6H), 2.17(s, 3H).

Elemental Analysis $C_{14}H_{17}Br_2N_3O_3S$ Calc.: % C, 36.1; % H, 3.68; % N, 9.01; % S, 6.88 Found: % C, 35.9; % H, 3.98; % N, 8.89; % S, 6.86

22. Preparation of 2-Benzylthio-6,8-dichloro[1,2,4]triazolo[1,5-a]pyridine 1-((1-Imidazolylthionyl)amino)-2-imino-3,5-dichloropyridine (1.0 g, 3.5 mmol) was combined with n-butanol (10 mL) in a round bottom flask and heated to 100° C. with stirring. Benzyl chloride (0.48 mL, 4.2 mmol) was added and the mixture was heated at reflux with stirring for 1.5 hour. The volatiles were then removed by evaporation under reduced pressure and the solid residue obtained was triturated with hexane (20 mL), water (20 mL), and hexane (20 mL). The resulting solid was washed with hexane on a filter and dried to obtain 0.80 g (74 percent of theory) of the title compound as a pale yellow solid melting at 115°–116° C.

Elemental Analysis $C_{13}H_9N_3Cl_2S$ Calc.: % C, 50.3; % H, 2.92; % N, 13.6; % S, 10.3 Found: % C, 49.4; % H, 2.32; % N, 13.8; % S, 10.1

$^1$H NMR (DMSO-d$_6$): 9.28(s, 1H) 8.08(s, 1H), 7.46(d, 2H, J=7.2), 7.27–7.31(m, 3H), 4.50(s, 2H); $^{13}$C NMR (DMSO-d$_6$): 164.9, 148.2, 137.2, 130.5, 128.9, 128.5, 127.4, 126.5, 119.7, 119.4, 34.7.

2-Benzylthio-6,8-dibromo[1,2,4]triazolo[1,5-a]pyridine was prepared similarly. The product was obtained in 84 percent yield as a pale yellow solid melting at 123°–124° C.

Elemental Analysis $C_{13}H_9N_3Br_2S$ Calc.: % C, 39.1; % H, 2.27; % N, 10.5; % S, 8.03 Found: % C, 38.8; % H, 2.34; % N, 10.6; % S, 8.17

$^1$H NMR (DMSO-d$_6$): 9.34(d, 1H, J=1.8), 8.23(d, 1H, J=1.5), 7.47(d, 2H, J=6.9), 7.25–7.33(m, 3H); 4.49(s, 2H).

23. Preparation of 2-Benzylthio-6-bromo-8-methoxy[1,2,4]triazolo[1,5-a]pyridine 2-Benzylthio-6,8-dibromo[1,2,4]triazolo[1,5-a]pyridine (9.5 g, 23.8 mmol) was mixed with acetonitrile (50 mL) in a round bottom flask. Sodium methoxide (13.1 mL of 25 percent solution in methanol, 57.1 mmol) was added and the mixture was heated at reflux for 2 hours. Glacial acetic acid (10 mL) was added and the entire reaction mixture was poured into a mixture of ice and water (300 mL). The brown precipitate that formed was recovered by filtration and dried.

This was chromatographed on silica gel eluting with a 1:1 mixture of ethyl acetate and hexane. Product-containing fractions were combined and concentrated under reduced pressure to obtain 6.58 g (80 percent of theory) of the title compound as a pale yellow solid.

Elemental Analysis $C_{14}H_{12}N_3BrSO$ Calc.: % C, 48.0; % H, 3.45; % N, 12.0; % S, 9.75 Found: % C, 47.8; % H, 3.36; % N, 11.9; % S, 9.22

$^1$H NMR (DMSO-$d_6$): 8.85(d, 1H, J=1.5), 7.42(d, 2H, J=7.5), 7.23–7.31(m, 4H), 4.46(s, 2H), 3.97(s, 3H).

2-Benzylthio-6-chloro-8-methoxy[1,2,4]triazolo[1,5-a]pyridine was prepared similarly. The product was obtained in 87 percent yield as a tan solid melting at 125°–126° C.

$^1$H NMR (DMSO-$d_6$): 8.84(d, 1H, J=1.5), 7.46(d, 2H, J=6.9) 7.26–7.36(m, 3H), 7.24(d, 1H, J=1.5), 4.50(s, 2H), 4.02(s, 3H).

2-Benzylthio-6-chloro-8-ethoxy[1,2,4]triazolo[1,5-a]pyridine was prepared similarly. The product was obtained in 100 percent yield as a pale orange oil. $^1$H NMR (DMSO-$d_6$) : 8.83(d, 1H, J=1.2), 7.45(d, 2H, J=7.2), 7.26–7.34(m, 3H), 7.22(d, 9H, J=1.2), 4.49(s, 2H), 4.28(q, 2H, J=7.2), 1.41(t, 3H, J=6.9).

24. Preparation of 2-Benzylthio-5,8-dichloro[1,2,4]triazolo[1,5-a]pyridine

A mixture of 9.9 g (0.10 mol) of copper(I) chloride with 300 mL of acetonitrile was prepared and 8.7 mL (6.8 g 0.066 mol) of 90 percent t-butyl nitrite was added with stirring. After 10 min 9.5 g (0.033 mol) of 8-amino-2-benzylthio-5-chloro[1,2,4]triazolo[1,5-a]pyridine was added and the reaction mixture was allowed to react with stirring for 3 days. The mixture was then diluted with dichloromethane and 2N aqueous hydrochloric acid, and after mixing this well, the phases were separated. The organic layer was washed with 2N aqueous hydrochloric acid and concentrated by evaporation under reduced pressure. The residue was chromatographed on silica gel eluting with dichloromethane to obtain 6.5 g (63 percent of theory) of the title compound as a yellow powder melting at 103°–104° C.

Elemental Analysis $C_{13}H_9Cl_2N_3S$ Calc.: % C, 50.3; % H, 2.92; % N, 13.6; % S, 10.3 Found: % C, 50.4; % H, 3.08; % N, 13.6; % S, 10.3

2-Benzylthio-8-chloro[1,2,4]triazolo[1,5-a]pyridine was prepared similarly from 8-amino-2-benzylthio-8-chloro[1,2,4]triazolo[1,5-a]pyridine. A 65 percent yield of this compound was obtained as a yellow powder melting at 82°–83° C.

Elemental Analysis $C_{13}h_{10}Cln_3S$ Calc.: % C, 56.6; % H, 3.66; % N, 15.2; % S, 11.6 Found: % C, 56.6; % H, 3.33; % N, 15.3; % S, 11.5

25. Preparation of 2-Benzylthio-8-chloro-5-methoxy[1,2,4]triazolo[1,5-a]pyridine 2-Benzylthio-5,8-dichloro[1,2,4]triazolo[1,5-a]pyridine (6.0 g, 0.019 mol) and 25 percent sodium methoxide in methanol (26.5 mL, 6.3 g, 0.116 mol) were combined in methanol and the mixture was heated to reflux for 2 hours. The mixture was then cooled, acidified with acetic acid, and concentrated by evaporation under reduced pressure. The residue was dissolved in dichloromethane and the solution was washed with water and concentrated by evaporation under reduced pressure The residue was triturated with hexane and the resulting solids were collected by filtration and dried to obtain 5.76 g (99 percent of theory) of the title compound as a light tan powder melting at 90°–91° C.

Elemental Analysis $C_{14}H_{12}ClN_3OS$ Calc.: % C, 55.0; % H, 3.96; % N, 13.7; % S, 10.5 Found: % C, 54.9; % H, 4.02; % N, 13.4; % S, 10.7

26. Preparation of 2-Benzylthio-8-bromo-5-chloro[1,2,4]triazolo[1,5-a]pyridine

Copper(I) bromide (4.9 g, 0.0034 mol) was combined with 200 mL of acetonitrile for 15 minutes and then 3.0 mL (2.3 g, 0.0023 mol) of 90 percent t-butyl nitrite was added and the mixture was stirred for a few minutes. 8-Amino-2-benzylthio-5-chloro[1,2,4]triazolo[1,5-a]pyridine (3.3 g, 0.0013 mol) was then added and the resulting mixture was stirred for 2 days. The resulting mixture was concentrated by evaporation under reduced pressure and the residue was chromatographed on silica gel eluting with dichloromethane. After the solvent of the product fractions was removed by evaporation under reduced pressure, the residue was mixed with hexane and the solid material was recovered by filtration and dried to obtain 2.6 g (56 percent of theory) of the title compound as a yellow powder melting at 122°–124° C.

Elemental Analysis $C_{13}H_9BrClN_3S$ Calc.: % C, 44.0; % H, 2.56; % N, 11.9; % S, 9.04 Found: % C, 43 9; % H, 2.59; % N, 11.9; % S, 8.86

27. Preparation of 2-Benzylthio-8-bromo-5-methoxy[1,2,4]triazolo[1,5-a]pyridine

2-Benzylthio-8-bromo-5-chloro[1,2,4]triazolo[1,5-a]pyridine (7.7 g, 0.0217 mol) and 25 percent sodium methoxide in methanol (19.9 mL, 4.7 g, 0.0868 mol) were mixed with 400 mL of methanol and the mixture was heated to reflux for 1.5 hours. It was then cooled and acidified with acetic acid. The volatiles were removed by evaporation under reduced pressure and the residue was dissolved in dichloromethane The resulting solution was washed with water and concentrated by evaporation under reduced pressure. The resulting residue was triturated with hexane and the solids obtained were recovered by filtration and dried to obtain 7.3 g (96 percent of theory) of the title compound as a light tan powder melting at 78°–79° C.

Elemental Analysis $C_{14}H_{12}BrN_3OS$ Calc.: % C, 48.0, % H, 3.45; % N, 12.0; % S, 9.16 Found: % C, 48.0; % H, 3.52; % N, 12.2; % S, 9.01

28. Preparation of 8-Amino-2-benzylthio-5,7-dibromo[1,2,4]triazolo[1,5-a]pyridine 8-Amino-2-benzylthio[1,2,4]triazolo[1,5-a]pyridine (14.0 g, 0.055 mol) was dissolved in dichloromethane and N-bromosuccinimide (9.7 g., 0.055 mol) was added with stirring at ambient temperature., After 1 hour, another 6.0 g of N-bromosuccinimide was added. The mixture was allowed to stir overnight and was then washed well with dilute aqueous sodium bisulfite solution and with water and concentrated by evaporation under reduced pressure The residue was chromatographed on silica gel eluting with 30 percent ethyl acetate in hexane to obtain 10.0 g (44 percent of theory) of the title compound as a dark gray powder melting at 116°–118° C.

29. Preparation of 2-Benzylthio-7-bromo-5-methoxy[1,2,4]triazolo[1,5-a]pyridine

2-Benzylthio-5,7-dibromo[1,2,4]triazolo[1,5-a]pyridine (11.6 g, 0.029 mol) and 25 percent sodium methoxide in methanol (13.0 mL, 3.1 g, 0.057 mol) were combined with 300 mL of acetonitrile and the mixture was heated to reflux with stirring for an hour. An additional 26 mL of 25 percent sodium methoxide in methanol was then added. After a 15-min reaction period, the mixture was acidified with acetic acid and the volatiles were removed by evaporation under reduced pressure. The residue was chromatographed on silica gel eluting with 20 percent ethyl acetate in hexane to obtain 4.97 g (49 percent of theory) of the title compound as a tan powder melting at 80°–82° C.

Elemental Analysis $C_{14}H_{12}BrN_3OS$ Calc.: % C, 48.0; % H, 3.45; % NM 12.0; % S, 9.16 Found: % C, 48.2; % H, 3.42; % N, 11.9; % S, 9.24

30. Preparation of 2-Chlorosulfonyl-5-chloro-7-methyl[1,2,4]triazolo[1,5-a]pyridine 2-Benzylthio-5-chloro-7-methyl-[1,2,4]triazolo[1,5-a]pyridine was mixed with equal volumes of dichloromethane and water with good stirring. Chlorine was added slowly at 3°–6° C. and the mixture allowed to react for another half hour. The organic layer was separated, dried over a mixture of magnesium and sodium sulfates, and concentrated by evaporation under reduced pressure. The residue was triturated with hexane and the resulting solids were recovered by filtration to obtain the title compound. A 91 percent of theory yield of this material was obtained as a pale yellow powder melting at 130°–132° C.

$^1$H NMR (CDCl$_3$): 7.62(s, 1H), 7.25(s, 1H), 2.57(s, 3H).

2-Chlorosulfonyl-5,7-dichloro[1,2,4]triazolo[1,5-a]pyridine was prepared similarly. A 100 percent yield of this compound was obtained as a Dale yellow solid melting at 164°–166° C.

Elemental Analysis C$_6$H$_2$Cl$_2$N$_3$O$_2$S Calc.: % C, 25.2; % H, 0.70; % N, 14.7; % S, 11.2 Found: % C, 25.2; % H, 0.65; % N, 14.4; % S, 10.9

6-Bromo-2-chlorosulfonyl-8-methoxy[1,2,4]triazolo[1,5-a]pyridine was prepared similarly. An 85 percent yield of this compound was obtained as a yellow solid.

$^1$H NMR (CDCl$_3$) 8.47(s, 1H), 7.11(s, 1H), 4.13(s, 3H).

6-Chloro-2-chlorosulfonyl-8-methoxy[1,2,4]triazolo[1,5-a]pyridine was prepared similarly. An 84 percent yield of this compound was obtained as an orange gum.

$^1$H NMR (CDCl$_3$): 8.38(d, 1H, J=1.8), 7.00(d, 1H, J=1.8), 4.13(s, 3H).

8-Chloro-2-chlorosulfonyl-5-methoxy[1,2,4]triazolo[1,5-a]pyridine was prepared similarly. A 96 percent yield of this compound was obtained as a tan powder melting at 147°–149° C.

8-Bromo-2-chlorosulfonyl-5-methoxy-[1,2,4]triazolo[1,5-a]pyridine was prepared similarly. A 90 percent yield of this compound was obtained as a tan powder melting at 120°–122° C. with decomposition.

7-Bromo-2-chlorosulfonyl-5-methoxy[1,2,4]triazolo[1,5-a]pyridine was prepared similarly. A 95 percent yield of this compound was obtained as a tan powder melting at 113°–115° C.

31. Preparation of N-(1-Ethyl-5-methyl-3-(trifluoromethyl)-4-pyrazolyl)-5-chloro-7-methyl[1,2,4]triazolo[1,5-a]pyridine-2-sulfonamide Pyridine (0.31 g (3.9 mmol)) and dimethyl sulfoxide (0.03 g (0.4 mmol)) were added to a solution of 1.0 g (3.9 mmol) of 2-chlorosulfonyl-5-chloro-7-methyl-[1,2,4]triazolo[1,5-a]pyridine and 0.76 g (3.9 mmol) of 4-amino-1-ethyl-5-methyl-3-(trifluoromethyl)pyrazole in 15 mL of acetonitrile at ambient temperature with stirring. After 18 hours, the volatiles were removed by evaporation under reduced pressure and the residue was partitioned between dichloromethane and water, stirring for 10 min before separation. The solids were recovered by filtration and washed with ether. They were then resuspended in water and the mixture stirred for 30 min. The solids were recovered by filtration, washed with ether, and dried under reduced pressure at 40° C. overnight. The resulting 1.24 g (68 percent of theory) of white powder melting at 224°–226° C. was the title compound.

Elemental Analysis C$_{14}$H$_{14}$ClF$_3$N$_6$O$_3$S Calc.: % C, 39.8; % H, 3.34; % N, 19.9; % S, 7.58 Found: % C, 39.6; % H, 3.17; % N, 20.0; % S, 7.49

32. Preparation of N-(1-Ethyl-5-methyl3-(trifluoromethyl)-4-pyrazolyl)-5-methoxy-7-methyl[1,2,4]triazolo[1,5-a]pyridine-2-sulfonamide A 25 percent solution of sodium methoxide in methanol (1.65 g, 5.4 mmol) was added to a solution of 1.14 g (2.70 mmol) of N-(1-ethyl-5-methyl-3-(trifluoromethyl)-4-pyrazolyl)-5-chloro-7-methyl[1,2,4]triazolo[1,5-a]pyridine-2-sulfonamide in 25 mL of dimethyl sulfoxide (DMSO) at ambient temperature with stirring. After 18 hours, 1.0 mL of acetic acid was added and the resulting mixture was concentrated by evaporation under reduced pressure. The residue was diluted with 25 mL of water and the resulting slurry was stirred for 10 min and then the insoluble solids collected by filtration, washed twice with 10 mL portions of water and then with 25 mL of ether, and dried under reduced pressure at 40° C. overnight. The resulting white solid, which amounted to 1.03 g (92 percent of theory) and melted at 230°–231° C. (d), was the title compound (Compound 2).

Elemental Analysis C$_{15}$H$_{17}$F$_3$N$_7$O$_3$S Calc.: % C, 43.1; % H, 4.10; % N, 20.1; % S, 7.66 Found: % C, 43.3; % H, 4.29; % M, 20.2; % S, 7.79

$^1$H NMR (CDCl$_3$): 10.21(brs, 1H), 7.32(s, 1H), 6.73(s, 1H), 4.12(s, 3H), 4.07(q, 2H, J=7.4), 2.48(s, 3H), 1.97(s, 3H), 1.27(t, 3H, J=7.4).

33. Preparation of N-(1-Ethyl-5-methyl-3-(trifluoromethyl)-4-pyrazolyl)-5-methoxy-7-methyl[1,2,4]triazolo[1,5-c]pyrimidine-2-sulfonamide Pyridine (0.32 g (4.0 mmol)) and dimethyl sulfoxide (0.03 g (0.4 mmol)) were added to a solution of 1.0 g (4.0 mmol) of 2-chlorosulfonyl-5-methoxy-7-methyl[1,2,4]triazolo[1,5-c]pyrimidine and 0.77 g (4.0 mmol) of 4-amino-1-ethyl-5-methyl-3-(trifluoromethyl)pyrazole in 15 mL of acetonitrile at ambient temperature with stirring. After 18 hours, the volatiles were removed by evaporation under reduced pressure and the residue was partitioned between dichloromethane and water, stirring for 10 min before separation. The solids were recovered by filtration and washed with ether. They were then resuspended in water and the mixture stirred for 30 min. The solids were recovered by filtration, washed with ether, and dried under reduced pressure at 40° C. overnight. The resulting 1.3 g (78 percent of theory) of white powder melting at 208°–209° C. was the title compound (Compound 1).

Elemental Analysis C$_{14}$H$_{16}$F$_3$N$_7$O$_3$S Calc.: % C, 40.1; % H, 3.85; % N, 23.4; % S, 7.64 Found: % C, 40.3; % H, 3.67; % N, 23.4; % S, 7.49

$^1$H NMR (CDCl$_3$): 10.39(brs, 1H), 7.47(s, 1H), 4.23(s, 3H), 4.10(q, 2H, J=7.3), 2.38(s, 3H), 2.08(s, 3H), 1.29 (t, 3H, J=7.3).

34. Evaluation of Postemergence Herbicidal Activity

Seeds of the desired test plant species were planted in Grace-Sierra MetroMix® 306 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7–21 days in a greenhouse with an approximately 15 hour photoperiod which was maintained at about 23°–29° C. during the day and 22°–28° C. during the night. Nutrients and water were added on a regular basis and supplemental lighting was provided with overhead metal halide 1000 Watt lamps as necessary. The plants were employed for testing when they reached the first or second true leaf stage.

A weighed amount, determined by the highest rate to be tested, of each test compound was placed in a 20 mL glass vial and was dissolved in 4 mL of a 97:3 v/v (volume/volume) mixture of acetone and dimethyl sulfoxide to obtain concentrated stock solutions If the test compound did not dissolve readily, the mixture was warmed and/or sonicated.

The concentrated stock solutions obtained were diluted with an aqueous mixture containing acetone, water, isopropyl alcohol, dimethyl sulfoxide, Atplus 411F crop oil concentrate, and Triton X-155 surfactant in a 48.5:399:10:1.5:1.0:0.02 v/v ratio to obtain spray solutions of known concentration. The solutions containing the highest concentration to be tested were prepared by diluting 2 mL aliquots of the stock solution with 13 mL of the mixture and lower concentrations were prepared by dilution of appropriate smaller portions of the stock solution. Approximately 1.5 mL aliquots of each solution of known concentration were sprayed evenly onto each of the test plant pots using a DeVilbiss atomizer driven by compressed air pressure of 2 to 4 psi (140 to 280 kiloPascals) to obtain thorough coverage of each plant. Control plants were sprayed in the same manner with the aqueous mixture. In this test an application rate of 1 ppm results in the application of approximately 1 g/Ha.

The treated plants and control plants were placed in a greenhouse as described above and watered by sub-irrigation to prevent wash-off of the test compounds. After 2 weeks the condition of the test plants as compared with that of the untreated plants was determined visually and scored on a scale of 0 to 100 percent where 0 corresponds to no injury and 100 corresponds to complete kill. Some of the compounds tested, application rates employed, plant species tested, and results are given in Table 2.

A weighed amount, determined by the highest rate to be tested, of each test compound was placed in a 20 mL glass vial and was dissolved in 8 mL of a 97:3 v/v (volume/volume) mixture of acetone and dimethyl sulfoxide to obtain concentrated stock solutions. If the test compound did not dissolve readily, the mixture was warmed and/or sonicated. The stock solutions obtained were diluted with a 99.9:0.1 mixture of water and Tween® 155 surfactant to obtain application solutions of known concentration. The solutions containing the highest concentration to be tested were prepared by diluting 4 mL aliquots of the stock solution with 8.5 mL of the mixture and lower concentrations were prepared by dilution of appropriate smaller portions of the stock solution. A 2.5 mL aliquot of each solution of known concentration was sprayed evenly onto the soil of each seeded pot using a Cornwall 5.0 mL glass syringe fitted with a TeeJet TN-3 hollow cone nozzle to obtain thorough coverage of the soil in each pot. Control pots were sprayed in the same manner with the aqueous mixture. A highest application rate of 4.48 Kg/Ha is achieved when 50 mg of test compound is emoloyed.

The treated Dots and control pots were placed in a greenhouse with an approximately 15 hr photoperiod which was maintained at about 23°–29° C. during the day and 22°–28° C. during the night. Nutrients and water were added on a regular basis and supplemental lighting was provided with overhead metal halide 1000 Watt lamps as necessary.

TABLE 2

POSTEMERGENCE HERBICIDAL ACTIVITY

| Cpd. No. | Rate, ppm | Soy-beans | Cot-ton | Lambs-quarters | Morning-glory | Wild Buckwheat | Black-grass | Barn-yard grass | Crab-grass | Giant foxtail | ROX Orange Sorghum | Wild Oats |
|---|---|---|---|---|---|---|---|---|---|---|---|---|
| 1 | 31.3 | 30 | 60 | 85 | 80 | 80 | 80 | 80 | 50 | 85 | 70 | 90 |
| 2 | 125 | 20 | 35 | 85 | 80 | 70 | 75 | 70 | 70 | 88 | 80 | 90 |
| 3 | 250 | 70 | 55 | 60 | 30 | 70 | 78 | 78 | 60 | 75 | 85 | 65 |
| 4 | 62.5 | 35 | 30 | 90 | 70 | 70 | — | 65 | 70 | 75 | 90 | 90 |
| 5 | 31.3 | 70 | 70 | 78 | 65 | 78 | 85 | 80 | 30 | 80 | 90 | 95 |
| 6 | 31.3 | 78 | 50 | 45 | 78 | 70 | 93 | 60 | 65 | 65 | 95 | 98 |
| 7 | 15.6 | 45 | 70 | 80 | 70 | 70 | 90 | 78 | 30 | 80 | 85 | 95 |
| 8 | 125 | 50 | 75 | 85 | 80 | 80 | 80 | 80 | 80 | 95 | 100 | 75 |
| 9 | 62.5 | 45 | 80 | 60 | 65 | 75 | 80 | 85 | 60 | 60 | 100 | 65 |
| 10 | 62.5 | 40 | 85 | 80 | 90 | 90 | 97 | 70 | 60 | 90 | 98 | 100 |
| 11 | 62.5 | 40 | 80 | 70 | 70 | 90 | 80 | 70 | 30 | 65 | 95 | 98 |
| 12 | 62.5 | 65 | 70 | 90 | 80 | 80 | 80 | 80 | 70 | 80 | 90 | 95 |
| 13 | 250 | 70 | 50 | 80 | 75 | 80 | — | 70 | 70 | 78 | 95 | 100 |
| 14 | 31.3 | 50 | 50 | — | 60 | 85 | 90 | 85 | 50 | 60 | 95 | 75 |
| 15 | 31.3 | 65 | 35 | 80 | 78 | 80 | 93 | 78 | 50 | 75 | 85 | 98 |
| 16 | 31.3 | 70 | 75 | 100 | 78 | 80 | 85 | 85 | 40 | 85 | 90 | 98 |
| 17 | 15.6 | 30 | 70 | 98 | 75 | 70 | 70 | 90 | 20 | 55 | 90 | 78 |
| 18 | 62.5 | 80 | 80 | 78 | 80 | 80 | 80 | 95 | 35 | 80 | 90 | 85 |

35. Evaluation of Preemergence Herbicidal Activity

Seeds of the desired test plant species were planted in a soil matrix prepared by mixing a loam soil which was composed of about 43 percent silt, 19 percent clay, and 38 percent sand and had a pH of about 8.1 and an organic matter content of about 1.5 percent and sand in a 70 to 30 ratio. The soil matrix was contained in plastic pots with a surface area of 161 square centimeters. When required to ensure good germination and healthy plants, a fungicide treatment and/or other chemical or physical treatment was applied.

The water was added by top-irrigation. After 3 weeks the condition of the test plants that germinated and grew as compared with that of the untreated plants that germinated and grew was determined visually and scored on a scale of 0 to 100 percent where 0 corresponds to no injury and 100 corresponds to complete kill or no germination. Some of the compounds tested, application rates employed, plant species tested, and results are given in Table 3.

TABLE 3

PREEMERGENCE HERBICIDAL ACTIVITY

| Cpd. No. | Rate, Kg/Ha | Soybeans | Cotton | Lambs-quarters | Pigweed | Black-grass | Barnyard grass | Crabgrass | Giant foxtail | ROX Orange Sorghum | Wild Oats |
|---|---|---|---|---|---|---|---|---|---|---|---|
| 1  | 0.070 | 10 | 50 | 98  | 95 | 90  | 90  | 75  | 98  | 85  | 80  |
| 2  | 0.070 | 15 | 20 | 90  | 80 | 85  | 85  | 60  | 95  | 85  | 80  |
| 3  | 0.14  | 0  | 0  | 20  | 80 | —   | 80  | 85  | 70  | 95  | 30  |
| 4  | 0.28  | 0  | 20 | —   | 40 | 100 | 98  | 100 | 98  | 100 | 70  |
| 5  | 0.14  | 20 | 0  | —   | 30 | 95  | 80  | 0   | 95  | 90  | 85  |
| 6  | 0.070 | 10 | 25 | —   | 0  | 85  | 70  | 35  | 80  | 95  | 85  |
| 7  | 0.070 | 10 | 30 | 85  | 95 | 90  | 70  | 75  | 95  | 95  | 75  |
| 8  | 0.28  | 20 | 0  | 100 | 90 | 70  | 98  | 78  | 95  | 100 | 65  |
| 9  | 0.14  | 10 | 10 | 90  | 98 | 70  | 90  | 65  | 82  | 100 | 20  |
| 10 | 0.14  | 10 | 30 | 95  | 0  | 100 | 100 | 100 | 85  | 100 | 50  |
| 11 | 0.28  | 10 | 35 | 95  | 80 | 100 | 100 | 75  | 100 | 100 | 50  |
| 12 | 0.14  | 20 | 75 | —   | 98 | 90  | 80  | 78  | 95  | 100 | 85  |
| 13 | 0.56  | 15 | 35 | —   | 0  | 100 | 80  | 80  | 90  | 98  | 100 |
| 14 | 0.035 | 30 | 30 | —   | 75 | —   | 85  | 65  | 80  | 98  | 30  |
| 15 | 0.070 | 10 | 35 | —   | 40 | 85  | 78  | 60  | 90  | 78  | 85  |
| 16 | 0.070 | 10 | 20 | —   | 78 | 80  | 78  | 50  | 95  | 90  | 80  |
| 17 | 0.28  | 0  | 60 | —   | 75 | 78  | 70  | 70  | 70  | 95  | 80  |
| 18 | 0.070 | 50 | 65 | —   | 55 | 95  | 55  | 50  | 78  | 100 | 70  |

What is claimed is:

1. An N-(1-ethyl-4-pyrazolyl)triazoloazine-2-sulfonamide compound of the formula:

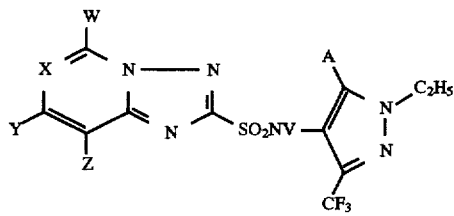

wherein

A represents H, $CH_3$, $OCH_3$, Cl, or Br; and

V represents H, $CO(C_1-C_4)$alkyl optionally singly to completely substituted with fluorine, $CO_2(C_1-C_4)$ alkyl, $CO_2(C_3-C_4)$alkenyl, $CO_2(C_3-C_4)$alkynyl, $CONH(C_1-C_4)$alkyl or $CON((C_1-C_4)alkyl)_2$; and either (a)

W represents $OCH_3$ or $OC_2H_5$;

X represents CH or N; and one of Y and Z represents Cl, Br, I, $OCH_3$, or $CH_3$ and the other represents H; or (b)

W and Y each represents H;

X represents C—Q and Q represents Cl, Br, I, $OCH_3$, or $CH_3$; and

Z represents $OCH_3$ or $OC_2H_5$; and when V represents H, the agriculturally acceptable salts thereof.

2. A compound according to claim 1 wherein V represents H.

3. A compound according to claim 1 wherein X represents N or CH.

4. A compound according to claim 3 wherein Y represents Cl, Br, or $CH_3$ and Z represents H or wherein Y represents H and Z represents $OCH_3$.

5. A compound according to claim 4 wherein Y represents $CH_3$ and Z represents H.

6. A compound according to claim 1 wherein A represents $CH_3$ or $OCH_3$.

7. A compound according to claim 6 which is one of N-(1-ethyl-5-methyl-3-(trifluoromethyl)-4-pyrazolyl)-5-methoxy-7-methyl-[1,2,4]triazolo[1,5-c]pyrimidine-2-sulfonamide, N-(1-ethyl-5-methoxy-3-(trifluoromethyl)-4-pyrazolyl)-5-methoxy-7-methyl [1,2,4]triazolo[1,5-c]pyrimidine-2-sulfonamide, and N-(1-ethyl-5-methyl-3-(trifluoromethyl)-4-pyrazolyl)-5-ethoxy-7-methyl[1,2,4]triazolo[1,5-c]pyrimidine-2-sulfonamide.

8. A compound according to claim 6 which is one of N-(1-ethyl-5-methyl-3-(trifluoromethyl)-4-pyrazolyl)-5-methoxy-7-methyl[1,2,4]triazolo[1,5-a]pyridine-2-sulfonamide and N-(1-ethyl-5-methyl-3-(trifluoromethyl)-4-pyrazolyl)-5-ethoxy-7-methyl[1,2,4]triazolo[1,5-a]pyridine-2-sulfonamide.

9. A composition comprising an herbicidally effective amount of an N-(1-ethyl-4-pyrazolyl)triazoloazine-2-sulfonamide compound of the formula:

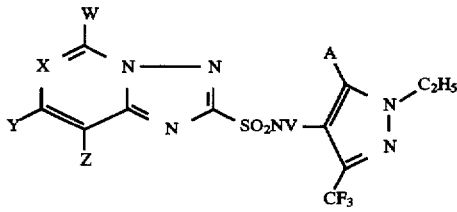

wherein

A represents H, $CH_3$, $OCH_3$, Cl, or Br; and

V represents H, $CO(C_1-C_4)$alkyl optionally singly to completely substituted with fluorine, $CO_2(C_1-C_4)$ alkyl, $CO_2(C_3-C_4)$alkenyl, $CO_2(C_3-C_4)$alkynyl, $CONH(C_1-C_4)$alkyl or $CON((C_1-C_4)alkyl)_2$; and either (a)

W represents $OCH_3$ or $OC_2H_5$;

X represents CH or N; and one of Y and Z represents Cl, Br, I, $OCH_3$, or $CH_3$ and the other represents H; or (b)

W and Y each represents H;

X represents C—Q and Q represents Cl, Br, I, $OCH_3$, or $CH_3$; and

Z represents $OCH_3$ or $OC_2H_5$; or when V represents H, the agriculturally acceptable salts thereof in combination with an agriculturally acceptable adjuvant or carrier.

10. A composition according to claim 9 wherein V represents H.

11. A composition according to claim 9 wherein X represents N or CH.

12. A composition according to claim 11 wherein Y represents Cl, Br, or $CH_3$ and Z represents H or wherein Y represents H and Z represents $OCH_3$.

13. A composition according to claim 12 wherein Y represents $CH_3$ and Z represents H.

14. A composition according to claim 9 wherein A represents $CH_3$ or $OCH_3$.

15. A composition according to claim 14 which comprises one of N-(1-ethyl-5-methyl-3-(trifluoromethyl)-4-pyrazolyl)-5-methoxy-7-methyl[1,2,4]triazolo[1,5-c]pyrimidine-2-sulfonamide, N-(1-ethyl-5-methoxy-3-(trifluoromethyl)-4-pyrazolyl)-5-methoxy-7-methyl[1,2,4]triazolo[1,5-c]pyrimidine-2-sulfonamide, and N-(1-ethyl-5-methyl-3-(trifluoromethyl)-4-pyrazolyl)-5-ethoxy-7-methyl [1,2,4]triazolo[1,5-c]pyrimidine-2-sulfonamide.

16. A composition according to claim 14 which comprises one of N-(1-ethyl-5-methyl-3-(trifluoromethyl)-4-pyrazolyl)-5-methoxy-7-methyl[1,2,4]triazolo[1,5-a]pyridine-2-sulfonamide and N-(1-ethyl-5-methyl-3-(trifluoromethyl)-4-pyrazolyl)-5-ethoxy-7-methyl[1,2,4]triazolo[1,5-a]pyridine-2-sulfonamide.

17. A method of controlling undesirable vegetation which comprises applying to the vegetation or to the locus thereof an herbicidally effective amount of an N-(1-ethyl-4-pyrazolyl)triazoloazine-2-sulfonamide compound of the formula:

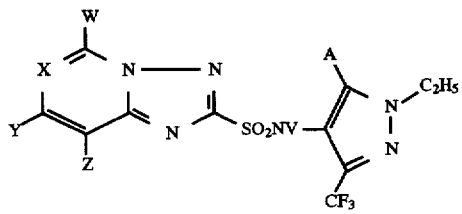

wherein

A represents H, $CH_3$, $OCH_3$, Cl, or Br; and

V represents H, $CO(C_1-C_4)$alkyl optionally singly to completely substituted with fluorine, $CO_2(C_1-C_4)$alkyl, $CO_2(C_3-C_4)$alkenyl, $CO_2(C_3-C_4)$alkynyl, $CONH(C_1-C_4)$alkyl or $CON((C_1-C_4)alkyl)_2$; and either (a)

W represents $OCH_3$ or $OC_2H_5$;

X represents CH or N; and one of Y and Z represents Cl, Br, I, $OCH_3$, or $CH_3$ and the other represents H; or (b)

W and V each represents H;

X represents C—Q and Q represents Cl, Br, I, $OCH_3$, or $CH_3$; and z represents $OCH_3$ or $OC_2H_5$; or when V represents H, an agriculturally acceptable salt thereof.

18. A method according to claim 17 wherein V represents H.

19. A method according to claim 17 wherein X represents N or CH.

20. A method according to claim 19 wherein Y represents Cl, Br, or $CH_3$ and Z represents H or wherein Y represents H and Z represents $OCH_3$.

21. A method according to claim 20 wherein Y represents $CH_3$ and Z represents H.

22. A method according to claim 17 wherein A represents $CH_3$ or $OCH_3$.

23. A method according to claim 22 wherein the compound is one of N-(1-ethyl-5-methyl-3-(trifluoromethyl)-4-pyrazolyl)-5-methoxy-7-methyl[1,2,4]triazolo[1,5-c]pyrimidine-2-sulfonamide, N-(1-ethyl-5-methoxy-3-(trifluoromethyl)-4-pyrazolyl)-5-methoxy-7-methyl[1,2,4]triazolo[1,5-c]pyrimidine-2-sulfonamide, and N-(1-ethyl-5-methyl-3-(trifluoromethyl)-4-pyrazolyl)-5-ethoxy-7-methyl[1,2,4]triazolo[1,5-c]pyrimidine-2-sulfonamide.

24. A method according to claim 22 wherein the compound is one of N-(1-ethyl-5-methyl-3-(trifluoromethyl)-4-pyrazolyl)-5-methoxy-7-methyl[1,2,4]triazolo[1,5-a]pyridine-2-sulfonamide and N-(1-ethyl-5-methyl-3-(trifluoromethyl)-4-pyrazolyl)-5-ethoxy-7-methyl[1,2,4]triazolo[1,5-a]pyridine-2-sulfonamide.

25. A method according to claim 17 wherein the compound is applied preplant or preemergence.

26. A method according to claim 25 wherein an amount of the compound selectively effective to soybeans is applied for the control of grassy weeds in a soybean crop.

27. A method according to claim 26 wherein the compound is applied in combination with a selectively effective amount of an herbicide which is useful for the control of broadleaf weeds in a soybean crop.

28. An N-1-ethyl-4-aminopyrazole compound of the formula:

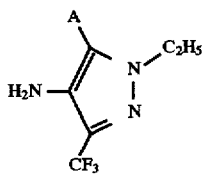

wherein A represents H, $CH_3$, $OCH_3$, Cl, or Br.

29. A compound according to claim 28 wherein A represents $CH_3$.

* * * * *

UNITED STATES PATENT AND TRADEMARK OFFICE
CERTIFICATE OF CORRECTION

PATENT NO. : 5,763,359
DATED : June 9, 1998
INVENTOR(S) : Mark J. Costales; William A. Kleschick; Robert J. Ehr, all of Indianapolis; Monte R. Weimer.

It is certified that error appears in the above-identified patent and that said Letters Patent is hereby corrected as shown below:

Abstract; Lines 2-4, "N-(1-ethyl-5-methyl-3--(trifluoromethyl)-4-pyrazoyl)-5-methoxy-7-methyl[1,2,4]-triazolo[1,5-c]pyrimidine-2-sulfonamide" should read --N-(1-ethyl-5-methyl-3-(trifluoromethyl)-4-pyrazolyl)-5--methoxy-7-methyl[1,2,4]triazolo[1,5-c]pyrimidine-2-sulfon-amide--.

Claim 17, line 18 (Col. 27, line 51), "V" should read --Y--.

Claim 17, line 21 (Col. 28, line 1), "z" should read --Z--.

Signed and Sealed this

Twenty-fourth Day of November, 1998

Attest:

BRUCE LEHMAN

*Attesting Officer*  *Commissioner of Patents and Trademarks*